United States Patent [19]

Pohndorf et al.

[11] Patent Number: 4,553,961
[45] Date of Patent: Nov. 19, 1985

[54] SUTURE SLEEVE WITH STRUCTURE FOR ENHANCING PACING LEAD GRIPPING

[75] Inventors: Peter J. Pohndorf, Miami Shores; Walter H. Wesner, Plantation, both of Fla.

[73] Assignee: Cordis Corporation, Miami, Fla.

[21] Appl. No.: 601,596

[22] Filed: Apr. 18, 1984

[51] Int. Cl.⁴ ............................................. A61M 25/00
[52] U.S. Cl. .................................... 604/175; 128/784; 128/419 P
[58] Field of Search ................... 128/DIG. 26, 419 P, 128/784–786; 604/171, 174, 175, 178, 180

[56] References Cited

U.S. PATENT DOCUMENTS

| | | | |
|---|---|---|---|
| 3,176,690 | 4/1965 | H'Doubler | 604/174 |
| 3,224,174 | 4/1966 | Wesbey et al. | 128/785 |
| 3,730,187 | 5/1973 | Reynolds | 604/178 |
| 3,821,957 | 7/1974 | Riely et al. | 604/178 |
| 4,114,626 | 9/1978 | Beran | 604/180 |
| 4,122,858 | 10/1978 | Schiff | 604/175 |
| 4,235,232 | 11/1980 | Spaven et al. | 604/178 |
| 4,278,092 | 7/1981 | Borsanyi et al. | 604/175 |
| 4,287,891 | 9/1981 | Peters | 604/174 |
| 4,332,259 | 6/1982 | McCorkle, Jr. | 128/786 |
| 4,425,670 | 1/1984 | Figuera | 3/1.5 |
| 4,437,475 | 3/1984 | White | 128/785 |

Primary Examiner—William E. Kamm
Attorney, Agent, or Firm—Henry W. Collins; Thomas R. Vigil

[57] ABSTRACT

A suture sleeve and associated gripping enhancing structure which extend longitudinally of an elongate axis of the suture sleeve which has a lumen therein and received over a lead body of a pacing lead. The gripping enhancing structure is radially compressible with the suture sleeve upon the tying of sutures around the suture sleeve to facilitate gripping of the lead body by the suture sleeve and/or gripping enhancing means. The gripping enhancing structure can be formed within and integral with the suture sleeve, or can be a separate thermoplastic part which is insert molded into the suture or which is received on and around the suture sleeve.

26 Claims, 9 Drawing Figures

SUTURE SLEEVE WITH STRUCTURE FOR ENHANCING PACING LEAD GRIPPING

BACKGROUND OF THE INVENTION

1. Field of the Invention

The present invention relates to a suture sleeve having a gripping enhancing structure. The gripping enhancing structure may be insert molded into a suture sleeve or may be formed integrally with the suture sleeve or attached to the suture sleeve. The suture sleeve is adapted to be secured to a ligated vein or underlying tissue during implantation of a pacing lead body within a body and the gripping enhancing structure facilitates secure fixing of the lead body in the suture sleeve at the time of implantation of the lead.

2. Description of the Prior Art

Heretofore, in the implantation of a pacing lead in an atrium or ventricle of a heart, a surgeon makes an incision at the venous site of choice. Then, a pacing lead is inserted into the right or left cephalic vein or the right external jugular vein near a pocket site chosen for a pacer or pacemaker unit containing a pulse generator. Now a tip electrode of the lead is moved through the vein and into an atrium or ventricle of the heart and fixed in place. After determining that the electrode position is satisfactory, the lead is connected to a pacer unit to be implanted in the pocket.

Next, an elastomeric suture sleeve, which is movable on the lead, is grasped at the tapered end and slid to a location where it is desirable to fasten the lead to tissue or to a ligated vein.

Examples of structures for securing a catheter or lead body to tissue or a ligated vein are disclosed in the following U.S. Patents:

The Reynolds U.S. Pat. No. 3,730,187 discloses a split collar which is C-shaped in cross-section and which has a plurality of sharp teeth or prongs that can grip the outer surface of a catheter when it is adjustably positioned in a desired location. A suture material is embedded within the collar and exits at the opening of the C in the C-shaped collar.

The Riely et al. U.S. Pat. No. 3,821,957 discloses a tubular body having four slits in the tubular body so that four arms can be folded out therefrom to form a retention slide for a catheter or tube.

The H'Doubler U.S. Pat. No. 3,176,690 discloses a catheter having tabs or flanges projecting therefrom which have openings therein for receiving a suture for securing to the skin of a patient.

The Peters U.S. Pat. No. 4,287,891 discloses a surgical safety holding device which is adapted to be fixed externally of a body to the body of a patient and fitted with a body tube. The device is used for securing the body tube against displacement. The device includes two tubular members which are telescoped together, which are rotatable relative to each other and which define a bore therein for receiving the body tube.

The Schiff U.S. Pat. No. 4,122,858 discloses an adapter for use with an intra-aortic balloon or similar device which facilitates insertion and positioning of the device and is designed to fit within a synthetic graft which is sutured, for example, to an artery. An annular groove is provided in the adapter, permitting the graft to be tightly held thereto in the region of the groove, with the device within the graft being able to freely slide therein for enabling proper positioning of the device. An insert is shown in combination with a suture groove. However, the insert is not resilient and only the catheter walls are formed of a resilient material.

As will be described in greater detail hereinafter, the suture sleeve with gripping enhancing structure of the present invention provides a resilient device which, when placed over a pacing lead body, grips the lead body when sutures are applied around the device to keep the device in place on the lead body as well as providing a structure which may be sutured to keep the lead body in place without interfering with the integrity of the lead body.

SUMMARY OF THE INVENTION

According to the invention there is provided a suture sleeve assembly comprising a suture sleeve made of soft elastomeric material and means associated with the suture sleeve for enhancing gripping of a lead body by the suture sleeve, said suture sleeve comprising a tubular sleeve having a throughbore adapted to receive a pacing lead body body and two spaced apart outer annular suture receiving grooves each adapted to receive a suture therein to fix said assembly to a pacing lead, said gripping enhancing means being made of a material which is different than the material of the suture sleeve and which is stiff but flexible, and said gripping enhancing means being positioned to extend within and longitudinally of an elongate axis of said suture sleeve in the area of and between said annular grooves thereby to disperse any stress placed upon said suture sleeve when sutures are tied in said annular grooves, and said suture sleeve assembly being radially compressible upon the placement and tying of a suture around said suture sleeve assembly in each annular groove to facilitate generally uniform gripping of the lead body by said suture sleeve assembly along the length of said gripping enhancing means.

There is further provided a suture sleeve assembly comprising a suture sleeve made of soft elastomeric material and means associated with the suture sleeve for enhancing gripping of a lead body by the suture sleeve, said suture sleeve comprising a tubular sleeve having a throughbore adapted to receive a pacing lead body and two spaced apart outer annular suture receiving grooves each adapted to receive a suture therein to fix said assembly to a pacing lead, said gripping enhancing means being made of a material which is identical to the material of the suture sleeve, said gripping enhancing means being located in the area beneath said annular grooves and said suture sleeve assembly being radially compressible upon the placement and tying of a suture around said suture sleeve assembly in each annular groove to facilitate generally uniform gripping of the lead body by said gripping enhancing means of said suture sleeve assembly.

Still further there is provided a suture sleeve assembly comprising a suture sleeve made of soft elastomeric material and means associated with the suture sleeve for enhancing gripping of a lead body by the suture sleeve, said suture sleeve having a throughbore which is adapted to receive a pacing lead body, said gripping enhancing means comprising a C-shaped sleeve that is made of a material which is different than the material of the suture sleeve and which is stiff but flexible, said C-shaped sleeve being received around the outer surface of said suture sleeve and having two spaced apart outer, partially annular, suture receiving grooves each adapted to receive a suture therein to fix said assembly to a pacing lead, said C-shaped sleeve being positioned to extend longitudinally of an elongate axis of said suture sleeve thereby to disperse any stress placed upon said suture sleeve when sutures are tied in said partially annular grooves, and said suture sleeve assembly being radially compressible upon the placement and tying of a suture around said suture sleeve assembly in each annular groove to facilitate generally uniform gripping of the lead body by said suture sleeve assembly along the length of said C-shaped sleeve.

It is to be noted that the gripping enhancing structure can be formed within and integral with the suture sleeve, or can be a separate thermoplastic part which is insert molded into the sleeve or which is received on and around the sleeve.

DESCRIPTION OF THE PREFERRED EMBODIMENTS

Figure 1:
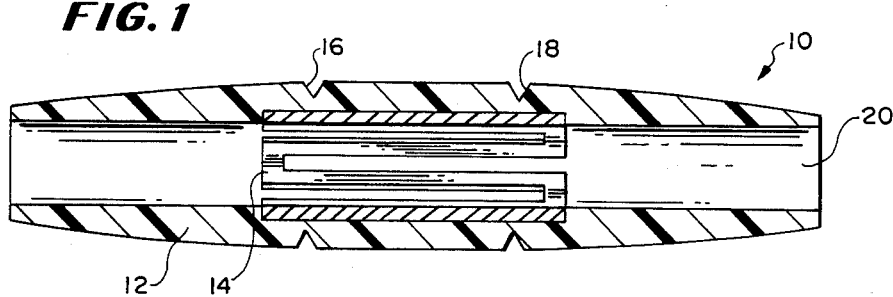
FIG. 1 is an axial sectional view of a suture sleeve having one embodiment of the gripping enhancing structure of the present invention insert molded therein.

Referring now to the drawings in greater detail, there is illustrated in FIG. 1, one embodiment 10 of a suture sleeve 12 with gripping enhancing structure 14 of the present invention received therein. In this particular embodiment 10, the suture sleeve 12 is made of a silastic material while the gripping enhancing structure 14 is formed of a thermoplastic material, such as rigid nylon. The gripping enhancing structure 14 is insert molded to the silastic sleeve 12 at a position centrally disposed within the silastic sleeve 12 with the ends of the gripping enhancing structure 14 located within the sleeve 12 beneath two circumferential/annular suture receiving grooves 16 and 18 formed in the outer periphery of the suture sleeve 12. The suture receiving grooves 16 and 18 are provided to receive sutures (not shown) therein once the sleeve 12 is fed over a pacing lead body (not shown). The lead body is received within a throughbore 20 formed within the suture sleeve 12.

Figure 2:
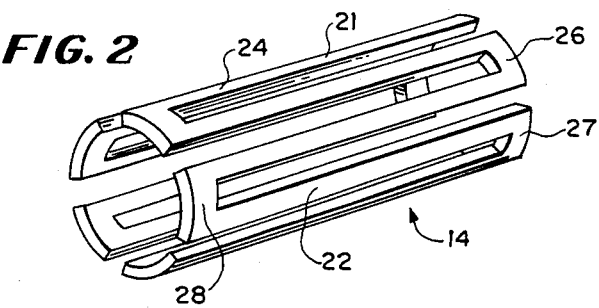
FIG. 2 is a perspective view of the gripping enhancing structure shown in FIG. 1.

As better illustrated in FIG. 2, the gripping enhancing structure 14 comprises a framework 21 of an undulating or sinuous, continuous rib 22 including axially extending segments 24, or simply axial segment 24, and short partially circular segments 26, or simply short circular segment 26. Each short circular segment 26 connects an adjacent pair of axial segments 24 at one end 27 or 28 of the framework 21. Each axial segment 24 of the sinuous rib 22 is spaced an equal distance from each of the adjacent axial segments 24 and this formation allows for compressibility of framework 21 against a lead body.

Figure 3:
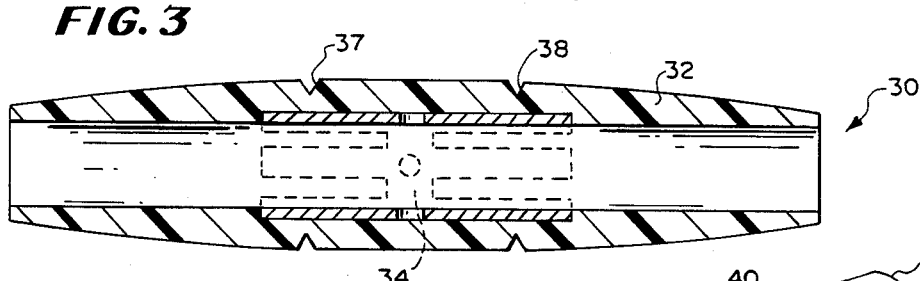
FIG. 3 is an axial sectional view of a suture sleeve having another embodiment of the gripping enhancing structure of the present invention insert molded therein.

Turning now to FIG. 3, there is illustrated therein, another embodiment 30 of a suture sleeve 32 with a gripping enhancing structure 34 constructed according to the teachings of the present invention.

The suture sleeve 32 is identical to the suture sleeve 12 illustrated in FIG. 1 and therefore will not be described in greater detail here. However, it will be understood that the second embodiment 30 includes a gripping enhancing structure 34 which is insert molded into the suture sleeve 32 in a manner similar to the insert molding of the gripping enhancing structure 14 into the suture sleeve 12 illustrated in FIG. 1. Also, it will be noted that the gripping enhancing structure 34 is positioned beneath annular suture receiving grooves 37,38 formed in the outer periphery of the suture sleeve 32.

Figure 4:
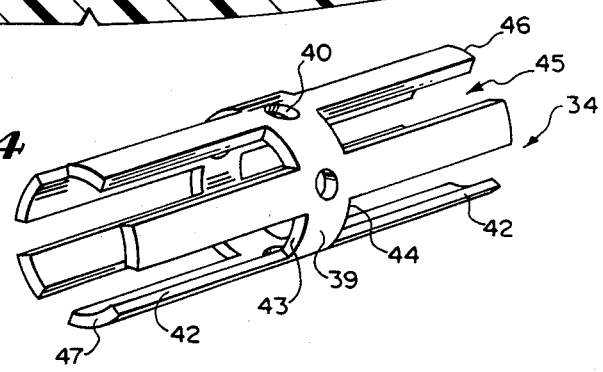
FIG. 4 is a perspective view of the gripping enhancing structure shown in FIG. 3.

As shown in FIG. 4, the gripping enhancing structure 34 comprises a collar 39 with spaced apart holes 40 therein. These holes 40 are filled with silicone during insert molding of the structure 34 to the sleeve 32 to help hold the structure 34 in place within the sleeve 32.

Extending axially from this central collar 39 are fingers or flanges 42 which extend, five on each side, from both side edges 43,44 of the collar 39 parallel to the axis of a central opening 45 within the collar 39. An equal spacing of the fingers 42 about the circumferential periphery is again provided to allow for flexing of the outer ends 46 of fingers 42 on one side of collar 39 and outer ends 47 of fingers 42 on the other side of collar 39 when sutures are received and tied within suture receiving grooves 37,38 in the sleeve 32 and tightened therearound.

Figure 5:
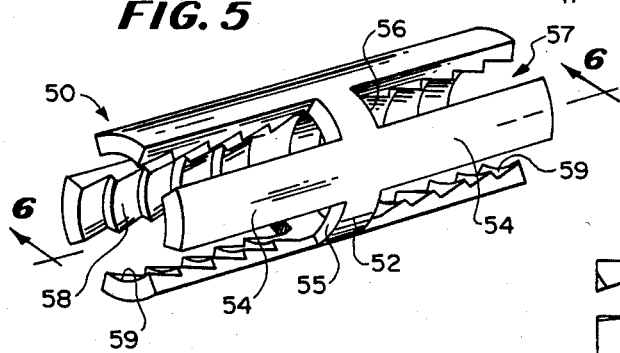
FIG. 5 is a perspective view of a further embodiment of the gripping enhancing structure of the present invention.

Referring now to FIG. 5, there is illustrated therein another embodiment of the gripping enhancing structure of the present invention which is generally identified by reference numeral 50 and which is similar to the structure 34 shown in FIG. 4. The structure 50 comprises a central collar 52 having four fingers or flanges 54 extending perpendicularly from opposite side edges 55,56 of the collar 52 coaxial with a central opening 57 in the collar 52. To enhance gripping, the fingers or flanges 54 have ramp teeth 58 extending transversely of each finger 52 on the inwardly facing surface 59 of each finger 54 as best shown in FIG. 6.

Figure 6:
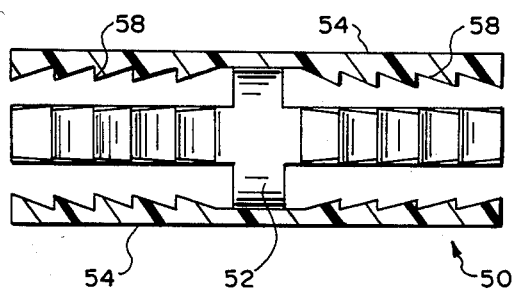
FIG. 6 is an axial sectional view of the gripping enhancing structure shown in FIG. 5 and is taken along line 6—6 of FIG. 5.

From FIG. 6, it will be seen that the teeth 58 have a ramp configuration so that their upwardly inclined edges face toward the ends of each finger or flange 54. The teeth 58 provide a gripping fit of a suture sleeve and the gripping enhancing structure 50 to a lead body (not shown) to prevent movement of the lead body within the suture sleeve such as suture sleeve 32. This embodiment is particularly useful under circumstances where the lead body is wet and would otherwise slide easily within the suture sleeve.

Figure 7:
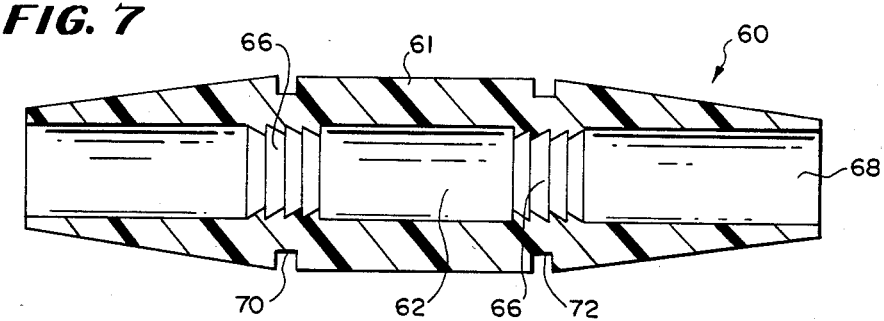
FIG. 7 is an axial sectional view of yet another embodiment of the gripping enhancing structure of the present invention formed integral within a suture sleeve.

Referring now to FIG. 7, there is illustrated therein another embodiment 60 of a suture sleeve 61 with a gripping enhancing structure 62 constructed according to the teachings of the present invention. In this embodiment 60, the gripping enhancing structure 62 is formed integral with the suture sleeve 61. Here, the suture sleeve 61 is provided with wiper type gasket teeth 66 within a central lumen 68 of the sleeve 61 in an area between and radially inwardly of two spaced apart annular suture receiving grooves 70,72 on the outer periphery of the sleeve 61. These teeth 66 not only allow for flexibility of the sleeve 61 in the area of the suture receiving grooves 70,72 but also serve to keep a lead body (not shown) dry in the area bounded by the gasket teeth 66. Further, by forming the gasket teeth to have an inner diameter of approximately 0.003 inch less than the diameter of the lead body to be received therein, a friction fit of the sleeve 61 onto the lead body is established.

Figure 8:
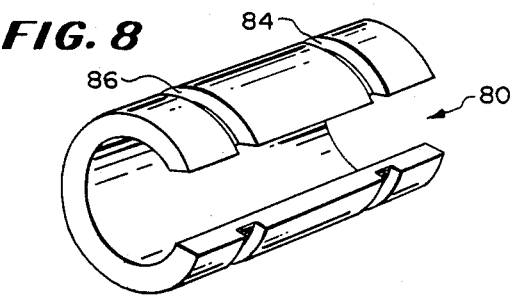
FIG. 8 is a perspective view of another embodiment of the gripping enhancing structure of the present invention in which the gripping enhancing structure is adapted to be received around a suture sleeve.
Figure 9:
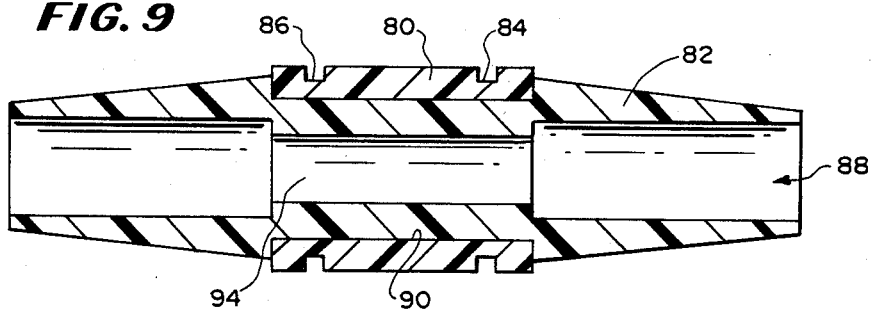
FIG. 9 is an axial sectional view of a suture sleeve with the gripping enhancing structure shown in FIG. 8 received therearound.

Referring now to FIG. 8, there is disclosed therein yet another gripping enhancing structure 80 for use with a suture sleeve 82 (FIG. 9). The gripping enhancing structure 80 is a partially cylindrical thin-walled, molded thermoplastic collar 80, the cross section of which resembles a "C". Provided around the outer periphery of the collar 80 are two, spaced apart, partially annular, suture receiving grooves 84 and 86. The suture sleeve 82 shown in FIG. 9 for receiving the collar has a lumen 88 therein and a wide, semi-annular, reduced-in-diameter slot 90 that is adapted to receive the collar 80. The gripping enhancing is enhanced not only by the collar 80 but also by a reduced-in-diameter lumen portion 94 in the middle of the suture sleeve beneath the wide slot 90.

As better illustrated in FIG. 9, the collar 80 is received around the suture sleeve 82 about the external circumference of the sleeve 82 and within the slot 90. The reduced-in-diameter portion 94 of the lumen 88 of the sleeve 82 is formed to have a diameter equal to or slightly less than the diameter of the lead body over which it is to be received. Once the lead body has been inserted into the sleeve 82, the collar 80 has been placed around the sleeve 82 and sutures have been tied into the suture receiving grooves 84 and 86, a friction fit of the sleeve 82 and collar 80 to the lead body is obtained.

From the foregoing description it will be apparent that the suture sleeve with the gripping enhancing structure of the present invention in its various forms, has a number of advantages, some of which have been described above and others of which are inherent in the invention. For example, the suture sleeve with gripping enhancing structure can be used with lead bodies of varying diameter since the throughbore or lumen within the suture sleeve may be of varying dimensions as well. Further, since compression of the suture sleeve is possible to upon tying of sutures therearound, the fit of the sleeve to the lead body need not be exact. Further, where a friction fit of the sleeve to the lead body is desirable, the friction fit is adjustable, such adjustment being dependent upon how tightly the sutures are tied into the suture receiving grooves. Still further, suture sleeves with the gripping enhancing structure of the present invention may be used with leads that are wet or with leads wherein dryness of the lead within a particular location is desired.

Also, it is to be understood that modifications can be made to the suture sleeve with gripping enhancing structure of the present invention without departing from the teachings of the present invention. Accordingly, the scope of the invention is only to be limited as necessitated by the accompanying claims.

We claim:

1. A suture sleeve assembly comprising a suture sleeve made of soft elastomeric material and means associated with the suture sleeve for enhancing gripping of a lead body by the suture sleeve, said suture sleeve comprising a tubular sleeve having a throughbore adapted to receive a pacing lead body and two spaced apart outer annular suture receiving grooves each adapted to receive a suture therein to fix said assembly to a pacing lead, said gripping enhancing means being made of a material which is different than the material of the suture sleeve and which is stiff but flexible, and said gripping enhancing means being positioned to extend within and longitudinally of an elongate axis of said suture sleeve in the area of and between said annular grooves thereby to disperse any stress placed upon said suture sleeve when sutures are tied in said annular grooves, and said suture sleeve assembly being radially compressible upon the placement and tying of a suture around said suture sleeve assembly in each annular groove to facilitate generally uniform gripping of the lead body by said suture sleeve assembly along the length of said gripping enhancing means.

2. The assembly of claim 1 wherein said gripping enhancing means comprise a cylindrical flexible framework within a suture sleeve forming a cylindrical envelope.

3. The assembly of claim 2 wherein said framework is defined by an undulating or sinuous arrangement of a continuous rib extending in axial segments connected by short circular segments.

4. The assembly of claim 2 wherein said framework is made of a thermoplastic material.

5. The gripping enhancing means of claim 4 wherein said thermoplastic material is nylon.

6. The assembly of claim 2 wherein said framework is insert molded into the suture sleeve.

7. The assembly of claim 1 wherein said gripping enhancing means comprise a framework within the suture sleeve including a collar and flexible fingers extending axially outwardly from the collar so as to form a cylindrical envelope.

8. The assembly of claim 7 wherein a plurality of fingers extend axially from each side of the ring or collar shaped member.

9. The assembly of claim 7 wherein said framework is made of a thermoplastic material.

10. The assembly of claim 9 wherein said thermoplastic material is nylon.

11. The assembly of claim 7 wherein said collar has a plurality of radially extending holes therein spaced around the circumference of said collar.

12. The assembly of claim 7 including four circumferentially spaced apart fingers.

13. The assembly of claim 7 including five circumferentially spaced apart fingers.

14. The assembly of claim 7 wherein said axially extending fingers have teeth in a sawtooth formation on the internal surfaces thereof with the points of said teeth directed outwardly from the center along the fingers.

15. The assembly of claim 7 wherein said framework is made of a thermoplastic material.

16. The assembly of claim 15 wherein said thermoplastic material is nylon.

17. The assembly of claim 7 wherein said framework is insert molded into the suture sleeve.

18. The assembly of claim 1 wherein said gripping enhancing means comprise at least two annular, inwardly extending, axially spaced, circular teeth formed on the inner cylindrical surface of said sleeve in the area of the suture receiving grooves, said teeth forming, in an axial cross-section, a sawtooth formation which is parallel to the axis of said sleeve and which extends radially and axially of said sleeve.

19. The assembly of claim 18 wherein said sleeve is formed of a silicone rubber material.

20. The assembly of claim 1 wherein said gripping enhancing means and said suture sleeve are a single integrally formed structure.

21. The assembly means of claim 20 wherein said suture sleeve is formed of a silicone rubber material.

22. A suture sleeve assembly comprising a suture sleeve made of soft elastomeric material and means associated with the suture sleeve for enhancing gripping of a lead body by the suture sleeve, said suture sleeve comprising a tubular sleeve having a throughbore adapted to receive a pacing lead body and two spaced apart outer annular suture receiving grooves each adapted to receive a suture therein to fix said assembly to a pacing lead, said gripping enhancing means being made of a material which is identical to the material of the suture sleeve, said gripping enhancing means being located in the area beneath said annular grooves and said suture sleeve assembly being radially compressible upon the placement and tying of a suture around said suture sleeve assembly in each annular groove to facilitate generally uniform gripping of the lead body by said gripping enhancing means of said suture sleeve assembly.

23. A suture sleeve assembly comprising a suture sleeve made of soft elastomeric material and means associated with the suture sleeve for enhancing gripping of a lead body by the suture sleeve, said suture sleeve having a throughbore which is adapted to receive a pacing lead body, said gripping enhancing means comprising a C-shaped sleeve that is made of a material which is different than the material of the suture sleeve and which is stiff but flexible, said C-shaped sleeve being received around the outer surface of said suture sleeve and having two spaced apart outer, partially annular, suture receiving grooves each adapted to receive a suture therein to fix said assembly to a pacing lead, said C-shaped sleeve being positioned to extend longitudinally of an elongate axis of said suture sleeve thereby to disperse any stress placed upon said suture sleeve when sutures are tied in said partially annular grooves, and said suture sleeve assembly being radially compressible upon the placement and tying of a suture around said suture sleeve assembly in each annular groove to facilitate generally uniform gripping of the lead body by said suture sleeve assembly alon the length of said C-shaped sleeve.

24. The assembly of claim 23 wherein the suture sleeve has a reduced-in-diameter outer wide annular slot therein sized to receive said C-shaped sleeve.

25. The assembly of claim 23 wherein said suture sleeve is made of a silastic material and said C-shaped sleeve is made of a thermoplastic material.

26. The assembly of claim 23 wherein said gripping enhancing means further includes a wide reduced-in-diameter portion within the suture sleeve, said reduced-in-diameter portion having a diameter less than the diameter of the pacing lead body received therein.

* * * * *